(12) United States Patent
Chaung et al.

(10) Patent No.: US 10,117,929 B1
(45) Date of Patent: *Nov. 6, 2018

(54) NUCLEIC ACID-BASED ADJUVANT AND PORCINE VACCINE COMPOSITION INCLUDING THE SAME

(71) Applicant: National Pingtung University Of Science And Technology, Neipu (TW)

(72) Inventors: Hso-Chi Chaung, Neipu (TW); Guan-Ming Ke, Neipu (TW); Mei-Li Wu, Neipu (TW)

(73) Assignee: National Pingtung University of Science and Technology, Neipu, Pingtung (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/821,774

(22) Filed: Nov. 23, 2017

(51) Int. Cl.
| | | |
|---|---|---|
| *A61K 39/39* | (2006.01) | |
| *A61K 39/215* | (2006.01) | |
| *C07H 21/04* | (2006.01) | |
| *C12N 7/00* | (2006.01) | |
| *A61K 39/12* | (2006.01) | |
| *A61K 39/00* | (2006.01) | |

(52) U.S. Cl.
CPC .............. *A61K 39/39* (2013.01); *A61K 39/12* (2013.01); *A61K 39/215* (2013.01); *C07H 21/04* (2013.01); *C12N 7/00* (2013.01); *A61K 2039/5252* (2013.01); *A61K 2039/552* (2013.01); *A61K 2039/55561* (2013.01); *C12N 2710/16734* (2013.01); *C12N 2710/16771* (2013.01); *C12N 2770/20034* (2013.01); *C12N 2770/20071* (2013.01)

(58) Field of Classification Search
None
See application file for complete search history.

(56) References Cited

U.S. PATENT DOCUMENTS

| | | | | |
|---|---|---|---|---|
| 9,441,015 | B2 * | 9/2016 | Wu ....................... | C07K 14/005 |
| 2013/0309270 | A1 * | 11/2013 | von Andrian .......... | A61K 39/00 424/277.1 |
| 2016/0137699 | A1 * | 5/2016 | Wu ....................... | C07K 14/005 424/192.1 |

FOREIGN PATENT DOCUMENTS

| | | |
|---|---|---|
| TW | I351288 B | 11/2011 |
| TW | I554609 B | 10/2016 |

OTHER PUBLICATIONS

Geneseq database access No. BCQ55561 May 2016 by Wu et al in USPgPub 20160137699.*
Sequence alignment of instant SEQ ID No. 1 with SEQ ID No. 2 of U.S. Pat. No. 9,441,015, Sep. 13, 2016.*
Stegeman (Veterinary Microbiology. 1997; 55: 175-180).*
Baek et al. (Veterinary Immunology and Immonopathology. 2016; 174: 45-49).*
Lin et al. (Veterinary Immunology and Immunopathology. 2016; 172: 1-8).*
Heegaard et al. (Archives of Virology. 2011; 56: 183-202).*

* cited by examiner

*Primary Examiner* — Shanon A. Foley

(57) ABSTRACT

The present invention relates to a nucleic acid-based adjuvant and a porcine vaccine composition including the same. The nucleic acid-based adjuvant, which is a nucleic acid fragment consisting of a sequence listing as SEQ ID NO: 1, can be used as the nucleic acid-based adjuvant of a vaccine composition, thereby elevating the protective ability of the porcine vaccine composition.

1 Claim, 3 Drawing Sheets

Specification includes a Sequence Listing.

NUCLEIC ACID-BASED ADJUVANT AND PORCINE VACCINE COMPOSITION INCLUDING THE SAME

CROSS-REFERENCE TO SEQUENCE LISTING

The Sequence Listing text file created Mar. 14, 2018 (11 KB) and identified as "SP-4155-US-ST-F(ASCII)-amended.txt" is hereby incorporated by reference.

BACKGROUND

Field of Invention

The present invention relates to an animal vaccine composition. More specifically, the present invention relates to a porcine vaccine composition including a nucleic acid-based adjuvant with enhanced immune response.

Description of Related Art

The major components of porcine vaccine composition generally include an antigen and adjuvant. As for inactivated vaccines, chemical adjuvants, which have been common used in popular tradition, hardly trigger and provide adaptive immune response having sufficient protection unless there are supplemented with biological adjuvants. Among the biological adjuvants, oligodeoxynucleotides (ODN) containing CpG motif can stimulate cell activity of porcine lymphocytes and antigen-presenting cells, increase activation and maturation of antigen presentation of dentritic cell (DC) and promote Th1 immunity to specific antigens, thereby elevating immune cell activity and being an effective adjuvant.

Typically, the ODN containing CpG motif includes unmethylated CpG dinucleotides and several specific bases adjacent thereto. A nucleic acid fragment having the sequences of CpG dinucleotides and its adjacent bases can influence itself on the degree of the immunostimulatory effect. However, the nucleic acid fragment has activity only when it binds to specific receptor, and receptors of different animals have different protein structures. In the mammalian animals, the toll-like receptor-9 (TLR-9) of the innate immune system can be the receptor of ODN, for recognizing the main structure of the specific sequence of the immunostimulatory nucleic acid, so as to generate dangerous signal and induce the immune response. Therefore, the nucleic acid fragment of immunostimulatory sequence has animal species-specificity.

The protectivity of a porcine vaccine can be elevated by adding adjuvants therein; however, different vaccines including different antigens can induce immune responses in different levels of stimulation even those vaccines include the same adjuvant. Accordingly, there is an urgent need to confirm an adjuvant formulation favorably applied on different vaccines including different antigens for improving disadvantages of traditional or novel porcine vaccines.

SUMMARY

The invention provides a nucleic acid-based adjuvant consisting of a nucleic acid fragment having a sequence listing as SEQ ID NO: 1, and the nucleic acid-based adjuvant can be rapidly produced in mass by a prokaryotic expression system.

Moreover, the invention also provides a porcine vaccine composition including an antigen and a nucleic acid-based adjuvant, in which the nucleic acid-based adjuvant is consisted of a nucleic acid fragment having a sequence listing as SEQ ID NO: 1, so as to enhance immune activities of immunogenicity and cross-protection of the porcine vaccines.

According to the aforementioned aspect, the invention provides a nucleic acid-based adjuvant. In an embodiment, the nucleic acid-based adjuvant is consisted of a nucleic acid fragment having a sequence listing as SEQ ID NO: 1.

According to another aspect, the invention provides a porcine vaccine composition. In an embodiment, the porcine vaccine composition includes an antigen and a nucleic acid-based adjuvant, in which the nucleic acid-based adjuvant is consisted of a nucleic acid fragment having a sequence listing as SEQ ID NO: 1.

In the aforementioned embodiment, the antigen includes an inactivated virus strain or a recombinant protein. In an example, the inactivated virus strain comprises gE gene-knockout pseudorabies (PR) virus strain or chemically inactivated porcine epidemic diarrhea (PED) virus strain With application to the nucleic acid-based adjuvant and the porcine vaccine composition including the same, in which the porcine vaccine composition is added with the nucleic acid-based adjuvant, thereby effectively enhance immune activities of immunogenicity and cross-protection of the porcine vaccine.

It is to be understood that both the foregoing general description and the following detailed description are by examples, and are intended to provide further explanation of the invention as claimed.

BRIEF DESCRIPTION OF THE DRAWINGS

The disclosure can be more fully understood by reading the following detailed description of the embodiment, with reference made to the accompanying drawings as follows.

FIG. 3 illustrates a bar graph showing the GMT of neutralizing antibodies in pigs vaccinated by PEDV inactivated vaccine with or without the nucleic acid-based adjuvant X210 four weeks after vaccination according to an embodiment of the present invention.

FIGS. 4A to 4B illustrate bar graphs showing the GMT of neutralizing antibodies in serum (FIG. 4A) and colostrum (FIG. 4B) of pigs vaccinated by PEDV inactivated vaccine with or without the nucleic acid-based adjuvant X210 four weeks after vaccination.

DETAILED DESCRIPTION

Figure 1:
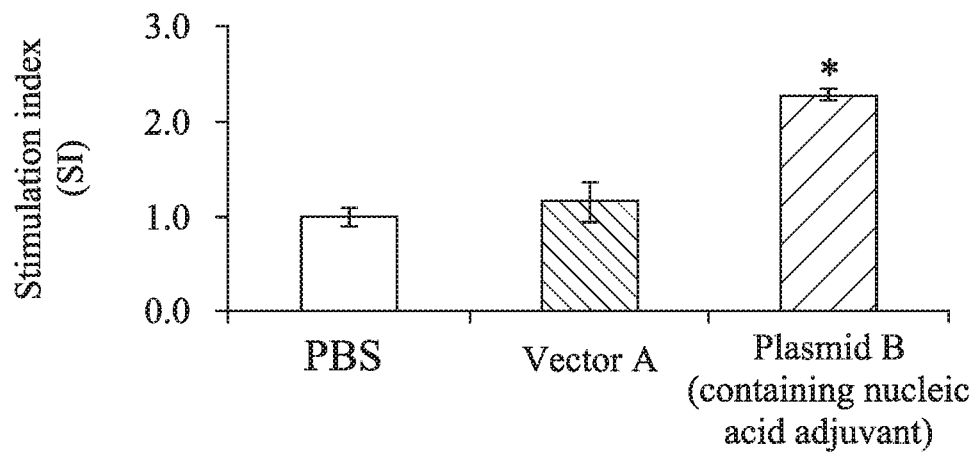
FIG. 1 illustrates a bar graph showing the stimulation index (SI) of cell proliferation in porcine peripheral blood mononuclear cells (PBMCs) stimulated by the nucleic acid-based adjuvant X210 according to an embodiment of the present invention.

Reference will now be made in detail to the present embodiments of the invention, examples of which are illustrated in the accompanying drawings. Wherever possible, the same reference numbers are used in the drawings and the description to refer to the same or like parts.

As aforementioned, the present invention provides a nucleic acid-based adjuvant and a porcine vaccine composition including the same, in which the nucleic acid-based adjuvant is added into the porcine vaccine, thereby effectively enhancing the immunogenicity and cross-protection of the porcine vaccine.

The nucleic acid adjuvants having immunostimulatory effects can be applied to many large domestic animals including cattle, pigs, sheep, goats and so on. The nucleic acid adjuvants having specific sequences can enhance activities of lymphocytes and antigen-presenting cells, increase antigen-presenting activation and maturation of the antigen-presenting cells, and promote responses of specific T-cell subgroups of the immune system against specific antigens in those animals.

The nucleic acid adjuvants having immunostimulatory effects can elevate immune responses by the mechanisms including (1) the increase of activation, maturation and antigen-presentation of the antigen-presenting cells; (2) increased migration of the antigen-presenting cells; (3) significantly increased expression of cell surface antigens of MHCII, CD40, CD80, CD86, IL-12 and the like on cell membranes of the mouse and human antigen-presenting cells; (4) the elevated responses of the antigen-presenting cells to T-cell subgroups against specific antigens, especially Th1 response; and (5) increased activity of $CD8^+$ T cells and induced cytotoxicity (CTL) of $CD8^+$ T cells against specific viruses or tumors. Therefore, the nucleic acid adjuvants having immunostimulatory effects themselves can produce protective immune response in the animal immune system against the infection of viruses, bacteria and extracellular parasites; alternatively, the nucleic acid adjuvants can enhance the immune responses of vaccines when combined with vaccines by activating B cells to generate antibodies and activating the antigen-presenting cells to secrete cytokines.

However, the sequences of the nucleic acid adjuvants having immunostimulatory effects are species-specific, and the sequence structures of the nucleic acid adjuvants for inducing better immunostimulatory effects are different among various species. Currently, most nucleic acid adjuvants are synthesized chemically, the ones effective in eliciting immune responses of animals are necessarily screened, assessed, confirmed by experiments, and then produced in mass.

Typically, the "nucleic acid-based adjuvant" as discussed hereinafter can include more than 200 base pairs of polynucleotide fragment or a recombinant plasmid containing the same. The polynucleotide fragment includes multiple CpG motifs with flanking functional sequences. The "multiple CpG motifs" as discussed hereinafter can be the multiple CpG motifs with flanking functional sequences connected head-to-tail. Generally, the oligonucleotides containing CpG motifs are species-specific, and the sequence structures of the CpG motifs for inducing better immunostimulatory effects are different among various species. Currently, the sequences of most effective immunoregulatory CpG motifs is different between human and mice, and thus specific CpG motifs effective in various species are necessarily confirmed by experiments.

The aforementioned CpG motifs of the oligonucleotides containing CpG motifs are unmethylated. A conventional chemical method is subjected to the synthesis of phosphorothioate (PTO)-modified oligonucleotides containing CpG motifs. The internucleotide phosphodiester bonds of the artificially synthesized oligonucleotides containing CpG motifs must be modified and non-bridging oxygen atoms is replaced with sulfur atoms (i.e. phosphorothioate modification), so that the rate of degrading the oligonucleotides containing CpG motifs by deoxyribonuclease (DNase) can be reduced. However, the conventional chemical method is time-consuming, expensive and hardly produces the oligonucleotides containing CpG motifs in mass.

The present invention is characterized by the design of porcine-specific nucleic acid sequence as the nucleic acid adjuvant. In an embodiment, the nucleic acid-based adjuvant can be exemplified as a nucleic acid fragment listed as the sequence of SEQ ID NO.: 1. In other embodiments, for the purpose of the large-scale production, various restriction enzyme sites can be added at two ends of the nucleic acid-based adjuvant depending on the actual requirements, followed by ligation into the corresponding restriction enzyme sites of commercial vectors, transformation into suitable host cells and mass production. The nucleic acid sequence designed by the present invention is manipulated easily, the nucleic acid-based adjuvant has stable property. After being evidenced by animal experimentations, various antigens of commercially porcine vaccine mixed with the nucleic acid-based adjuvant have significantly enhanced immune benefits.

In an embodiment, when the aforementioned nucleic acid-based adjuvant is applied in a porcine vaccine composition, the porcine vaccine composition can be consisted of an antigen and the nucleic acid-based adjuvant having a nucleic acid fragment as SEQ ID NO.:1.

In some embodiments, it is not intended to limit the aforementioned antigen. In some examples, the aforementioned antigen can include but be not limited to an inactivated virus strain or a recombinant antigen protein. In some instances, the inactivated virus strain can include but be not limited to gE gene-knockout pseudorabies (PR) virus strain or chemically inactivated porcine epidemic diarrhea (PED) virus strain. In application, it is not intended to limit the effective dose of the nucleic acid adjuvant. In the case of 4-week-old pigs, each pig is administered with a dose including $10^7$ $TCID_{50}$ of inactivated virus and 50 μg of the nucleic acid adjuvant. $TCID_{50}$ is an abbreviation of Tissue Culture Infection Dose 50. Virus infection titer is obtained by observation of the percentage of cytopathic effect (CPE) of virus-infected cells and calculation by a formula.

In other examples, the aforementioned recombinant protein can be exemplified as porcine reproductive and respiratory syndrome (PRRS) subunit vaccine. The PRRS subunit vaccine can be laboratory-developed PRRSV vaccine, in which the recombinant antigen can include a fusion subunit protein including a truncated N'-terminal decoy epitope glycoprotein GP5 of PRRSV, a linking sequence and membrane protein M. The fusion subunit protein is expressed by a gene expression system including a baculovirus expression vector (BEV) and its host insect cells. In application, it is not intended to limit the effective dose. In the case of 4-week-old pigs, each pig is administered with a dose including 50 μg of the recombinant antigen protein and 50 μg of the nucleic acid adjuvant.

In application, the aforementioned porcine vaccine composition, can be administered by intradermal injection, subcutaneous injection, intramuscular injection, intravenous injection or oral route. Specifically, animal experimentations prove that the porcine vaccine composition containing the nucleic acid-based adjuvant of the present invention is administered for a given period, for examples, after four weeks, thereby elevating the yield of neutralizing antibody in the serum and colostrum.

Thereinafter, various applications of the nucleic acid-based adjuvant and porcine vaccine composition including the same will be described in more details referring to several exemplary embodiments below, while not intended to be limiting. Thus, one skilled in the art can easily ascertain the essential characteristics of the present invention and, without departing from the spirit and scope thereof, can make various changes and modifications of the invention to adapt it to various usages and conditions.

Example 1: Design and Production of Nucleic Acid-Based Adjuvant

In this example, the nucleic acid-based adjuvant used in this example was a nucleic acid fragment having a sequencing listed as SEQ ID NO: 1, two ends of which can be added with restriction enzyme sites for ligating into commercial vectors.

In this example, the nucleic acid fragment having a sequence listed as SEQ ID NO: 1 can be chemically synthesized. For synthesizing the nucleic acid fragment of SEQ ID NO: 1, it alternatively has known restriction enzyme sites at its two ends, or it can be the nucleic acid fragment having a sequence listed as SEQ ID NO: 2, for example. Such nucleic acid fragment can be easily ligated into a commercial vector to form a recombinant plasmid, and then be mass-produced in a host cell. It should be clarified that, the nucleic acid fragment having a sequence listed as SEQ ID NO: 2 was merely an example as the nucleic acid-based adjuvant X210-1, rather than limiting the nucleic acid-based adjuvant of the present invention being defined by those examples. As understood by a person skilled in the art, appropriate restriction enzyme sites can be designed at its two ends of the nucleic acid fragment depending on the commercial vector that was being ligated with.

The restriction enzyme sites can be designed according to a vector that was used in mass production. In this example, the nucleic acid fragment of the nucleic acid-based adjuvant X210-1 has SpeI site at 5' end and XbaI site at 3' end.

And then, a commercial vector A, for example, pET vector series, can be provided, which has SpeI site, XbaI site and ScaI site. Afterward, the vector A can be ligated with the nucleic acid fragment at restriction enzyme sites of SpeI site and XbaI site, the nucleic acid fragment was inserted between SpeI site and XbaI site of the vector A to form a recombinant plasmid B. The recombinant plasmid B can be transformed into suitable bacteria for producing the nucleic acid-based adjuvant in mass.

The ligated plasmid was then transformed into DH5a competent cell. The successfully transformed cells were screened by conventional blue-white method and then cultured. The plasmids B were extracted in small scale from those cells, and the nucleic acid fragment in the plasmid B was obtained by digestion of restriction enzymes SpeI and XbaI. The sequence of the nucleic acid fragment was analyzed and identified by electrophoresis and DNA sequencing. The nucleic acid fragment can be served as the nucleic acid-based adjuvant X210 and evaluated as below.

Example 2: Screening and Evaluation of Nucleic Acid-Based Adjuvant Applied on Porcine Peripheral Blood Mononuclear Cells (PBMC)

2.1 Culture of Porcine PMBCs

Whole bloods of 4-week-old two-breed specific pathogen free (SPF) pigs were collected. Next, heparin (as an anticoagulant, 10 IU/mL blood) was added into the whole blood, and the diluted blood was slowly added over 3 mL Ficoll-Hypaque solution in another tube, for forming a clear interface between the blood layer and Ficoll-Hypaque layer. And then, the tube was centrifuged and layered at 500 rpm by a commercial horizontal centrifuge for 10 minutes, and the PBMC layer was took and washed trice by RPMI1640 solution (centrifugation at 1000 rpm for 10 minutes). Finally, the PBMC cells had the cell density of $1\times10^7$ cells/mL adjusted by RPMI1640 complete medium and were seeded into 24-well cell culture plate.

2.2 Detection of Cell Surface Antigen Expression

PBS (as control group) or 20 µg/20 µL/well of DNA of vector A (without the nucleic acid fragment X210) or the recombinant plasmid B (containing the nucleic acid fragment X210) was added to each well including 1 mL of PBMC cell suspension. Each treatment group was made in duplicates and cultured in 5% $CO_2$ at 37° C. for 48 hours. And then, those cells were labeled by 10 µL/well BrdU reagent and incubated for another 24 hours. After removing the supernatants of each well by centrifugation at 1000 rpm for 10 minutes, 200 µL/well of FixDenat solution was added to each well and placed at room temperature for 30 minutes. Later, the FixDenat solution was removed, 100 µL/well of anti-BrdU-pod working solution was added to each well and placed at room temperature for 90 minutes. Afterwards, the anti-BrdU-pod working solution was removed and each well was washed by 300 µL/well thrice. Following, the wash solution was removed, 100 µL/well of substrate solution was added to each well and placed at room temperature for 5 minutes of developing color. Subsequently, the absorbance of each well at 370 nm of wavelength was detected by ELISA reader and resulted in FIG. 1.

Reference was made to FIG. 1, which was illustrates a bar graph showing the stimulation index (SI) of cell proliferation in porcine peripheral blood mononuclear cells (PBMCs) stimulated by the nucleic acid-based adjuvant X210 according to an embodiment of the present invention. The stimulation index (SI) was calculated by dividing a mean absorbance ($OD_{370nm}$) of all treated cells (treated with the vector DNA or the nucleic acid-based adjuvant X210) by a mean absorbance ($OD_{370nm}$) of untreated cells (i.e. PBS control group). Symbol "*" in FIG. 1 was referred to the mean having significant difference in comparison to the PBS control group ($P<0.05$) [triplicate for each group (n=3) and duplicated incubation. As shown in the result of FIG. 1, the nucleic acid-based adjuvant X210 effectively enhanced cell proliferation activity of porcine PBMC cells.

In addition, PBS (as control group) or 20 µg/20 µL/well of DNA of vector A (without the nucleic acid fragment X210) or the recombinant plasmid B (containing the nucleic acid fragment X210) was added to each well including 1 mL of PBMC cell suspension. Each treatment group was made in duplicates and cultured in 5% $CO_2$ at 37° C. for 24 hours. After incubation, the PBMC cells in each tube had the cell density of $5\times10^4$ cells/mL adjusted by PBS including 0.1% sodium azide and 1% fetal bovine serum. The porcine cell surface antigens MHC I$^+$, MHC II$^+$, MHC I$^+$MHC II$^+$ and CD80/86$^+$ of the cells were detected, whereas the cells were stained by monoclonal antibodies of mouse IgG1-PE and mouse IgG2a-FITC as isotype control groups. The cells were added and mixed well with monoclonal antibodies listed in Table 1 as primary antibodies respectively, followed by incubation on ice for 20 minutes in the dark. After the cells reacted to fluorescence-labelled monoclonal antibodies, the cell surface antigens of the cells were analyzed by flow cytometry (Coulter Epics Altra Flow Cytometry, Beckman Coulter, CA). However, the cell surface antigens of the cells that were reacted to other unlabeled primary antibodies were further reacted to fluorescence-labelled secondary antibodies and analyzed. The fluorescence intensity data of those cells was statistically assessed via commercial analysis software, for example, Expo 32 v1.0 MultiCOMP Software (Applied Cytometry Systems, Sheffield, UK), and listed in Table 2.

TABLE 1

| Hybridoma clone | Specificity | Isotype | Label | Manufacturers |
|---|---|---|---|---|
| Primary antibodies | | | | |
| 1E3[a] | Swine SLA-class 1 | $IgG_1$ | Purified | Pharmingen |
| 1053h2-18-1[a] | Swine SLA-DR | $IgG_{2a}$ | Purified | Pharmingen |
| hCTLA-4-mFc[b] | Swine CD80/86 | $IgG_{2a}$ | PE | Ancell |
| Secondary antibodies | | | | |
| A85-1[c] | Mouse $IgG_1$ | $IgG_1$ | PE | Pharmingen |
| R19-15[c] | Mouse $IgG_{2a}$ | $IgG_1$ | FITC | Pharmingen |

[a]Antibody to swine leukocyte antigen.
[b]Antibody to human leukocyte antigen cross-reaction with swine antigens.
[c]Secondary antibody to primary antibodies.

TABLE 2

| | Cell surface markers | | | |
|---|---|---|---|---|
| Treatments | $MHCI^+$ | $MHCII^+$ | $MHCI^+$ $MHCII^+$ | $CD80/86^+$ |
| PBS (Control) | 93.7 | 18.0 | 16.9 | 3.0 |
| Empty vector A DNA | 92.5 | 20.6 | 18.8 | 3.6 |
| Recombinant plasmid containing the nucleic acid fragment X210 | 93.1 | 26.3* | 24.3* | 3.7 |

Symbol "*" is referred to the group having significant difference in comparison to the PBS control group (P < 0.05 in triplicate).

As the results of Table 2, the recombinant plasmid B containing the nucleic acid fragment X210 could advantageously enhance the expression of MHC $II^+$ and MHC $I^+$MHC $II^+$ of porcine PBMCs.

3. Evaluation of Adjuvant Activity of Nucleic Acid-Based Adjuvant in Porcine Vaccine 3.1 Evaluation of Adjuvant Activity of Nucleic Acid-Based Adjuvant in Porcine Pseudorabies (PR) Vaccine Twelve 4-week-old commercial three-breed cross pigs were divided into three groups of (1) PR inactivated vaccine, (2) PR inactivated vaccine added with 50 μg of the nucleic acid-based adjuvant X210 and (3) control. Four weeks after vaccination, the whole bloods were collected for detecting titers of the neutralizing antibodies in the serum. The aforementioned PR vaccine was inactivated PR vaccine made of PRV-Bartha strain (natural deficiency in gE gene) by the laboratory of the inventors. In brief, the inactivated PR vaccine was produced by culturing PR virus to a titer of $10^7$ $TCID_{50}$, inactivating PR virus in 0.1% of formalin at 37° C. for 24 hours, and mixing the inactivated PR virus with ISA206 (Seppic Inc.) adjuvant in a weight ratio of 1:1.

The titers of the neutralizing antibodies in the sera were detected as follows. PRV-Bartha strain was used in this virus neutralization assay and cultured to 100 $TCID_{50}$/mL. The serum was incubated in a complement-free medium (in a water bath) at 56° C. for 30 minutes. Next, there were the two-fold serially diluted serum (including neutralizing antibodies) added in the first ten wells of a 96-well cell culture plate, there was no serum in the eleventh well as a positive control, and there was only DMEM medium in the twelfth well as a negative control. Immediately, the 100 $TCID_{50}$/mL of viral suspension was added into all wells of the 96-well cell culture plate and sensitized at 37° C. for 60 minutes, those infectious solutions were inoculated to porcine kidney cell line PK-15 in another 96-well cell culture plate. After incubation at 37° C. for 3 to 4 days, the cytopathic effect (CPE) was observed, geometric mean titer (GMT) of each group was calculated by total titers of neutralizing antibodies in the sera of each group as shown in FIG. 2.

Figure 2:
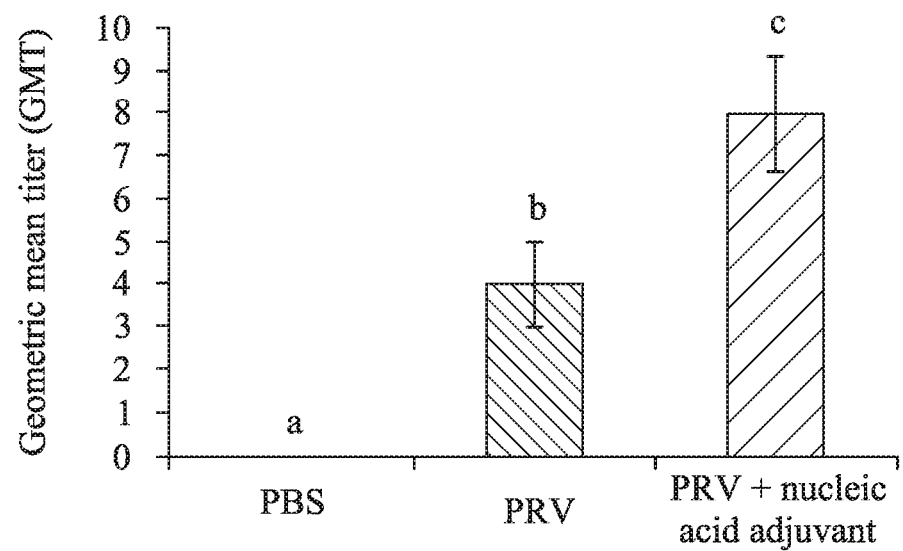
FIG. 2 illustrates a bar graph showing the geometric mean titer (GMT) of neutralizing antibodies in pigs vaccinated by PRV inactivated vaccine with or without the nucleic acid-based adjuvant X210 four weeks after vaccination according to an embodiment of the present invention.

Reference was made to FIG. 2, which illustrated a bar graph showing the geometric mean titer (GMT) of neutralizing antibodies in pigs vaccinated by PRV inactivated vaccine with or without the nucleic acid-based adjuvant X210 four weeks after vaccination according to an embodiment of the present invention. The pigs vaccinated with PBS were as the negative control group. In FIG. 2, different letters were referred to significant difference between two groups (P<0.05).

As the results of FIG. 2, the GMT in the serum of the pigs vaccinated by PR inactivated vaccine with the nucleic acid-based adjuvant X210 four weeks after vaccination was significantly greater than the one vaccinated by PR inactivated vaccine without the nucleic acid-based adjuvant X210.

3.2 Evaluation of Adjuvant Activity of Nucleic Acid-Based Adjuvant in Porcine Epidemic Diarrhea (PED) Vaccine on Pigs Eight 4-week-old commercial three-breed cross pigs were divided into three groups of (1) PED vaccine, (2) PED vaccine added with 50 μg of the nucleic acid-based adjuvant X210 and (3) control. Four weeks after vaccination, the whole bloods were collected for detecting titers of the neutralizing antibodies in the serum. The aforementioned PED vaccine was an inactivated whole virus vaccine in which the PED virus was isolated in the wild by the laboratory of the inventors. In brief, the inactivated PED vaccine was produced by culturing PED virus to a titer of $TCID_{50}$ $10^7$, inactivating PED virus in 2% of binary ethyleneimine (BEI) at 37° C. for 24 hours, diluting the inactivated PED virus with phosphate-buffered saline (PBS) to 1 mL of the total volume as one dose, and mixing the inactivated PED virus with ISA206 (Seppic Inc.) adjuvant in a weight ratio of 1:1.

The titers of the neutralizing antibodies in the sera were detected as follows. PED virus isolated in the wild by the laboratory of the inventor was used in this virus neutralization assay and cultured to 100 $TCID_{50}$/mL. The serum was incubated in a complement-free medium (in a water bath) at 56° C. for 30 minutes. Next, there were the two-fold serially diluted serum (including neutralizing antibodies) added in the first ten wells of a 96-well cell culture plate, there was no serum in the eleventh well as a positive control, and there was only DMEM medium in the twelfth well as a negative control. Immediately, the 100 $TCID_{50}$/mL of viral suspension was added into all wells of the 96-well cell culture plate and sensitized at 37° C. for 60 minutes, those infectious solutions were inoculated to vero cells in another 96-well cell culture plate. After incubation at 37° C. for 3 to 4 days, the cytopathic effect (CPE) was observed, geometric mean titer (GMT) of each group was calculated by total titers of neutralizing antibodies in the sera of each group as shown in FIG. 3.

Figure 3:
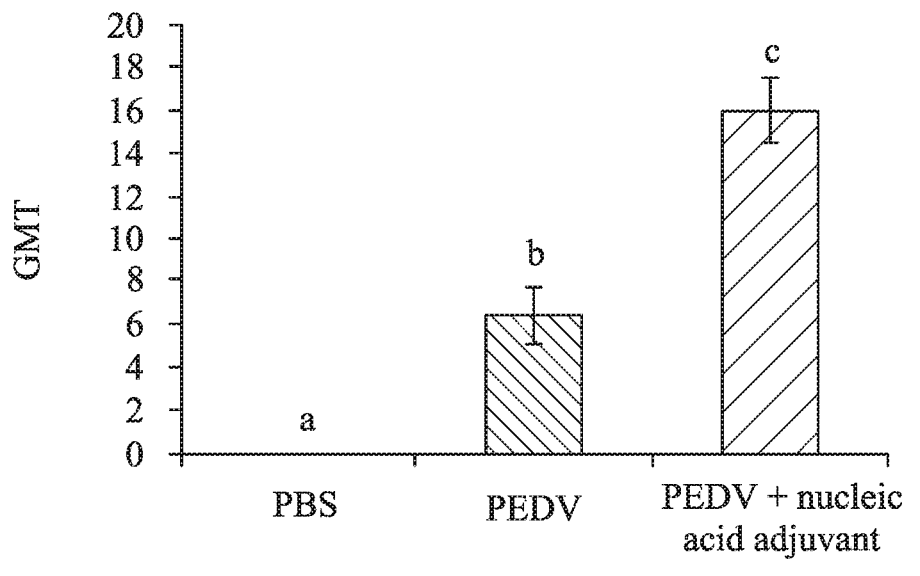

Reference was made to FIG. 3, which illustrated a bar graph showing the GMT of neutralizing antibodies in pigs vaccinated by PEDV inactivated vaccine with or without the nucleic acid-based adjuvant X210 four weeks after vaccination according to an embodiment of the present invention. The pigs vaccinated with PBS were as the negative control group. In FIG. 3, different letters were referred to significant difference between two groups (P<0.05).

As the results of FIG. 3, the GMT in the serum of the pigs vaccinated by PEDV inactivated vaccine with the nucleic acid-based adjuvant X210 four weeks after vaccination was significantly greater than the one vaccinated by PEDV inactivated vaccine without the nucleic acid-based adjuvant X210.

3.3 Evaluation of Adjuvant Activity of Nucleic Acid-Based Adjuvant in PED Vaccine on Pregnant Sows Eleven commercially pregnant sows were divided into two groups of (1) PED vaccine (n=6), (2) PED vaccine added with 50 μg of the nucleic acid-based adjuvant X210 (n=5). The sows were subjected to the first vaccination on six weeks before parturition, followed by the second vaccination on three weeks after the first vaccination. After parturition, the whole bloods and colostrum were collected for detecting titers of the neutralizing antibodies therein. The aforementioned PED vaccine was an inactivated whole virus vaccine in which the PED virus was isolated in the wild by the laboratory of the inventors. In brief, the inactivated PED vaccine was produced by culturing PED virus to a titer of $TCID_{50}$ $10^7$, inactivating PED virus in 0.1% of formalin at 37° C. for 24 hours, and mixing the inactivated PED virus with ISA206 (Seppic Inc.) adjuvant in a weight ratio of 1:1.

The titers of the neutralizing antibodies in the sera were detected as follows. PED virus isolated in the wild by the laboratory of the inventor was used in this virus neutralization assay and cultured to 100 $TCID_{50}$/mL. The serum was incubated in a complement-free medium (in a water bath) at 56° C. for 30 minutes. Next, there were the two-fold serially diluted serum (including neutralizing antibodies) added in the first ten wells of a 96-well cell culture plate, there was no serum in the eleventh well as a positive control, and there was only DMEM medium in the twelfth well as a negative control. Immediately, the 100 $TCID_{50}$/mL of viral suspension was added into all wells of the 96-well cell culture plate and sensitized at 37° C. for 60 minutes, those infectious solutions were inoculated to vero cells in another 96-well cell culture plate. After incubation at 37° C. for 3 to 4 days, the cytopathic effect (CPE) was observed, geometric mean titer (GMT) of each group was calculated by total titers of neutralizing antibodies in the sera of each group as shown in FIGS. 4A to 4B.

Figures 4A, 4B:
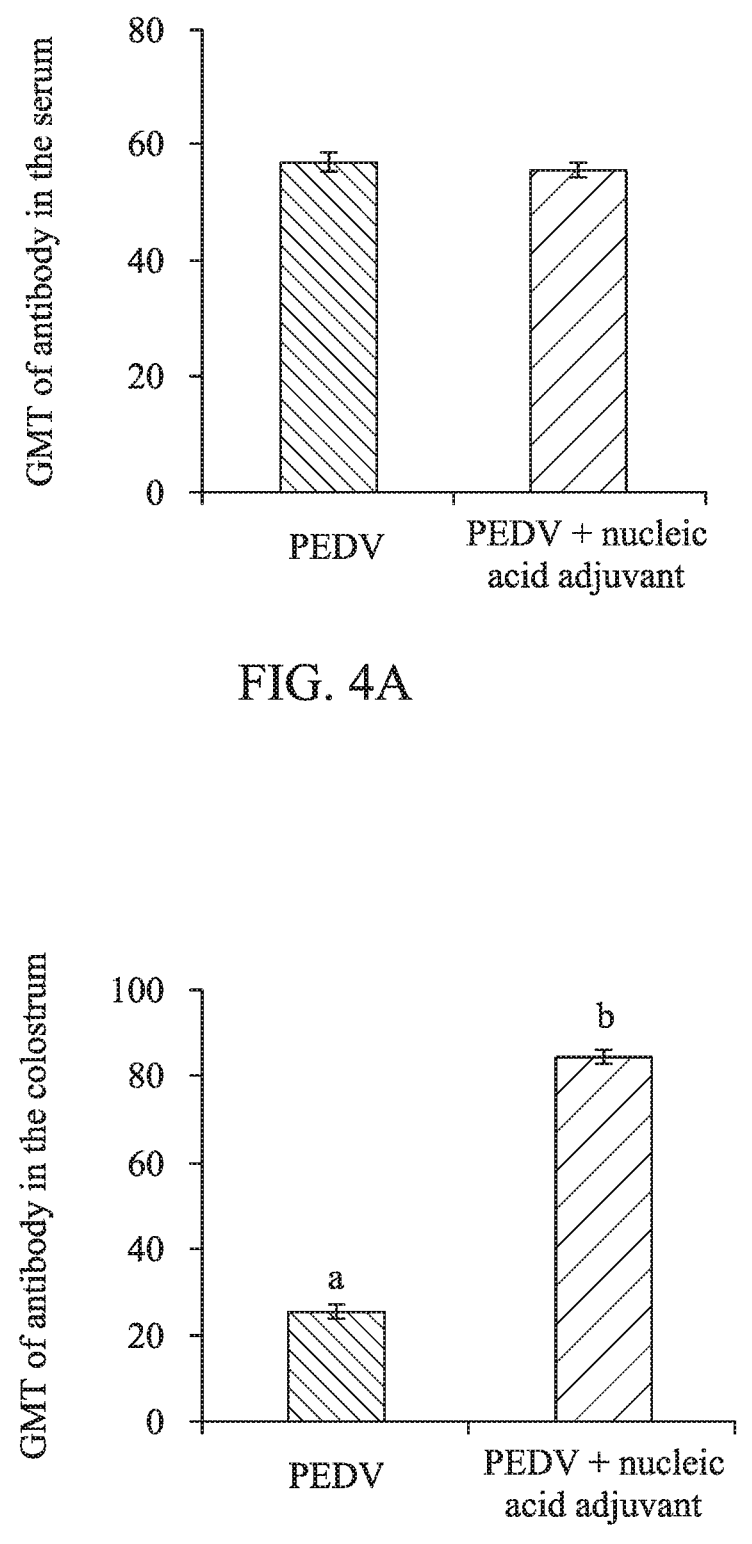

Reference was made to FIGS. 4A to 4B, which illustrated bar graphs showing the GMT of neutralizing antibodies in serum (FIG. 4A) and colostrum (FIG. 4B) of pigs vaccinated by PEDV inactivated vaccine with or without the nucleic acid-based adjuvant X210 four weeks after vaccination. In FIGS. 4A to 4B, different letters were referred to significant difference between two groups ($P<0.05$).

As the results of FIGS. 4A to 4B, the sows after two vaccinations, the GMT in the serum of the sows vaccinated by PEDV inactivated vaccine with the nucleic acid-based adjuvant X210 was insignificantly different from the one vaccinated by PEDV inactivated vaccine without the nucleic acid-based adjuvant X210 (as shown in FIG. 4A). However, the GMT in the colostrum of the sows vaccinated by PEDV inactivated vaccine with the nucleic acid-based adjuvant X210 was significantly greater than the one vaccinated by PEDV inactivated vaccine without the nucleic acid-based adjuvant X210, and the GMT in the colostrum had more than tripled (as shown in FIG. 4B).

In summary, it is necessarily supplemented that, specific nucleic acid adjuvants, specific kinds of porcine vaccine compositions, specific analysis models or specific evaluating methods are exemplified for clarifying the nucleic acid-based adjuvant and porcine vaccine composition including the same. However, as is understood by a person skilled in the art, other nucleic acid adjuvant, other kinds of porcine vaccine compositions, other analysis models or other evaluating methods can be also adopted in the nucleic acid-based adjuvant and porcine vaccine composition including the same without departing the spirit and scope of the present invention of the present invention rather than being limited as aforementioned. For example, the nucleic acid-based adjuvant and porcine vaccine composition of the present invention can be applied to other kinds of vaccines such as subunit vaccines, attenuated vaccines and the like, thereby beneficially elevating immune activities of immunogenicity and cross-protection of the porcine vaccines.

According to the embodiments of the present invention, the nucleic acid-based adjuvant and porcine vaccine composition including the same of the present invention are advantageous to add the porcine nucleic acid-based adjuvant into porcine vaccine compositions, thereby significantly enhance immune activities of immunogenicity and cross-protection of the porcine vaccine.

Although the present invention has been described in considerable detail with reference to certain embodiments thereof, other embodiments are possible. Therefore, the spirit and scope of the appended claims should not be limited to the description of the embodiments contained herein.

What is claimed is:

1. A porcine vaccine composition, comprising:
   an antigen, comprising an inactivated virus strain, wherein the inactivated virus strain comprises gE gene-knockout pseudorabies (PR) virus strain or chemically inactivated porcine epidemic diarrhea (PED) virus strain; and
   a nucleic acid-based adjuvant consisting of a nucleic acid fragment having a sequence listing as SEQ ID NO: 1.

* * * * *

SEQUENCE LISTING

```
<160> NUMBER OF SEQ ID NOS: 2

<210> SEQ ID NO 1
<211> LENGTH: 218
<212> TYPE: DNA
<213> ORGANISM: Artificial sequence
<220> FEATURE:
<223> OTHER INFORMATION: Nucleic acid-based adjuvant X210

<400> SEQUENCE: 1
tcgtcgaagt cgttttgggg ggtctagttc gtcgaaatcg atttggggggg tctagttcgt      60 cgaagtcgtt ttggggggtc tagttcgtcg aaatcgattt gggggggtcta gttcgtcgaa     120 gtcgttttgg ggggtctagt tcgtcgaaat cgatttgggg ggtctagttc gtcgaagtcg     180 ttttggggggg tctagttcgt cgaaatcgat ttggggggg                           218

<210> SEQ ID NO 2
<211> LENGTH: 230
```

```
<212> TYPE: DNA
<213> ORGANISM: Artificial sequence
<220> FEATURE:
<223> OTHER INFORMATION: Nucleic acid-based adjuvant X210-1

<400> SEQUENCE: 2
actagttcgt cgaagtcgtt ttgggggtc tagttcgtcg aaatcgattt gggggtcta       60 gttcgtcgaa gtcgttttgg ggggtctagt tcgtcgaaat cgatttgggg ggtctagttc    120
gtcgaagtcg ttttggggg tctagttcgt cgaaatcgat ttgggggtc tagttcgtcg     180 aagtcgtttt gggggtcta gttcgtcgaa atcgatttgg ggggtctaga                230
```